United States Patent
Stanley, III

[11] Patent Number: 6,024,095
[45] Date of Patent: Feb. 15, 2000

[54] CORNEAL HEAT AND STRETCH METHOD AND APPARATUS

[75] Inventor: H. Mark Stanley, III, San Leandro, Calif.

[73] Assignee: Proteus Therapeutics, Inc., San Leandro, Calif.

[21] Appl. No.: 09/058,334

[22] Filed: Apr. 10, 1998

[51] Int. Cl.[7] .................................................. A61B 17/32
[52] U.S. Cl. ................................ 128/898; 606/27; 607/98
[58] Field of Search ................................ 606/27, 31, 41, 606/42, 45, 50, 107, 4, 5, 6; 604/21, 22; 607/96, 98, 104; 128/898

[56] References Cited

U.S. PATENT DOCUMENTS

| | | |
|---|---|---|
| 13,953 | 12/1855 | Parish . |
| 72,108 | 12/1867 | Stephens . |
| 3,831,604 | 8/1974 | Neefe .......................................... 604/21 |
| 4,326,529 | 4/1982 | Doss et al. .................................. 606/41 |
| 4,381,007 | 4/1983 | Doss ........................................... 606/48 |
| 4,417,579 | 11/1983 | Soloviev et al. . |
| 4,619,259 | 10/1986 | Graybill et al. . |
| 4,688,570 | 8/1987 | Kramer et al. . |
| 4,744,362 | 5/1988 | Gründler . |
| 5,092,863 | 3/1992 | Schanzlin .................................... 606/5 |
| 5,108,412 | 4/1992 | Krumeich et al. . |
| 5,137,530 | 8/1992 | Sand ........................................... 606/5 |
| 5,616,139 | 4/1997 | Okamoto ..................................... 606/4 |
| 5,690,123 | 11/1997 | Medina . |
| 5,807,380 | 9/1998 | Dishler ........................................ 606/5 |
| 5,820,624 | 10/1998 | Yavitz ......................................... 606/4 |

OTHER PUBLICATIONS

Okuno, Tsutomu, "Thermal Effect of Infra–Red Radiation on the Eye: A Study Based on a Model", *Ann. Occup. Hyg.* (1991) 35(1):1–12.

Greene, Peter R., et al., "Scleral Creep vs. Temperature and Pressure in vitro", *Exp. Eye Res.* (1979) 29:527–537.

Warren, C. Gerald, et al., "Heat and Stretch Procedures: An Evaluation Using Rat Tail Tendon", *Arch. Phys. Med. Rehabil.* (1976) 57:122–126.

Ku, David N., et al., "Scleral Creep In Vitro Resulting from Cyclic Pressure Pulses: Applications to Myopia", *American Journal of Optometry & Physiological Optics* (1981) 58(7):528–535.

*Primary Examiner*—Michael Peffley
*Attorney, Agent, or Firm*—Karl Bozicevic; Bozicevic, Field & Francis LLP

[57] ABSTRACT

A method and apparatus to alter the shape of the cornea of an eye provides for heating a portion of the cornea to a temperature not exceeding the collagen shrinkage temperature, and applying a pressure differential to a portion of the cornea. The combined effect of elevated temperature and stretching forces leads to permanent residual strains in preferred directions, and thus to a permanent new shape of the cornea. The method is applicable to the correction or reduction of myopia, hyperopia, and astigmatism.

13 Claims, 7 Drawing Sheets

CORNEAL HEAT AND STRETCH METHOD AND APPARATUS

FIELD OF THE INVENTION

This invention relates to the field of ocular refractive procedures, specifically to a method of changing the curvature of the cornea of the eye.

BACKGROUND OF THE INVENTION

The condition of ametropia, in which images are not focused properly on the retina due to some refractive error in the eye, is pervasive in the general human population. Depending on the specific population considered, from 25% to 50% of persons have some degree of ametropia. The most common treatment for this condition is to place a corrective lens in the optical path, e.g. spectacles or contact lenses. Since conventional corrective measures have serious drawbacks, such as inconvenience and discomfort, there is substantial activity in the field of ophthalmology devoted to correcting ametropia by altering the optics of the eye itself. Most of this activity is concentrated on altering the cornea, which is the strong transparent membrane covering the central anterior portion of the eye.

The cornea contributes the greatest amount of refraction to the overall optical system of the eye due to its highly curved surface. Accordingly, small changes in corneal curvature can produce substantial changes in the focus of the eye. The cornea has five structural layers: epithelium, Bowman's membrane, stroma, Descemet's membrane, endothelium. The main load-bearing structures in the cornea are the uniform-diameter (about 30 nm) collagen fibrils within the many (several hundred) lamellae of the stroma. Much of the activity thus far has focused on altering the structure of the stroma within the cornea.

Several surgical methods have been used to alter the refractive properties of the cornea. A first surgical approach, Radial Keratotomy (RK), uses radial incisions to weaken the paracentral cornea in the circumferential direction by severing some collagen fibrils. Thus, this procedure can lead to circumferential expansion and consequent flattening of the optical zone in the central cornea. Another surgical approach removes layers of the stroma in specific patterns to achieve a "sculpting" of the corneal surface. Such removal can be by a keratome (knife) as in Automated Lamellar Keratoplasty (ALK), or by a laser, as in Photorefractive Keratectomy (PRK) and Laser in-situ Keratomileusis (LASIK). In PRK, material is ablated by laser directly from the anterior surface, thus destroying Bowman's layer and associated nerve endings. In LASIK, a flap of the cornea is first cut and folded back, so that only stromal layers are ablated. PRK, ALK, and LASIK all result in a thinned cornea. Thus, the remaining layers of the cornea must support the intraocular pressure. As a result, the optical effect of these surgeries depends in part on the stress-strain behavior of the remaining material.

Each of the surgical methods has serious side effects. The wounds from RK take several months to heal, and the resultant scarring tends to scatter light, leading to the perception of a "starburst" effect. RK, PRK, ALK, LASIK, and their variants are invasive or destructive, require time for wound healing, alter the natural structure of the cornea, offer limited predictability and stability, and often require similarly invasive corrections to maintain or improve the corrective alterations.

A non-surgical method of altering the shape of the cornea is through thermokeratoplasty, which heats selected locations of the cornea to at least the "collagen shrinkage temperature", causing the collagen fibrils to contract to about one-third their original length. Initially, heated wires were applied to the cornea, but it was found that the resulting collagen shrinkage was not stable, possibly due to the healing response of the tissue. Other methods of thermokeratoplasty have been proposed, such as using microwave radiation, radiofrequency antennae, ultrasound transducers, and lasers. The wide use of thermokeratoplasty was hindered, however, by the high temperature necessary for shrinkage of the collagen fibrils. Such high temperatures may permanently damage the more sensitive components of the cornea, especially the endothelium.

There remains a need for a safe, effective, non-invasive method of permanently altering the shape of the cornea to correct ametropia. There is also a need for an apparatus designed to practice this method of altering corneal shape.

SUMMARY OF THE INVENTION

A method and apparatus for non-invasively altering corneal curvature to correct ametropia by the combined application of heat and pressure differential is disclosed. The invention features an apparatus with a means for heating a selected portion of the cornea, and a means for the application of a pressure differential (e.g. suction) to a selected portion of the cornea. The apparatus uses the simultaneous combination of heat and suction to permanently stretch some of the collagen fibrils within the cornea, resulting in a change in the shape of the cornea and thus the focus of the eye. The invention also features a method for simultaneously combining heat and suction to cause a permanent change in the shape of the cornea by causing a stretching of the collagen fibrils within the eye.

The apparatus of the present invention may apply the heat and the suction simultaneously to the same area of the eye. Alternatively, heat may be applied to one area while a pressure differential is applied to another, possibly overlapping, area or heat may be applied followed by suction within a sufficiently short period of time that the eye remains heated to a point where it can be permanently deformed with pressure. The application of both heat and suction may be done cyclically, and may vary in the ratio of heating cycles to suction cycles. For example, each heat cycle may correspond to a single suction cycle. Alternatively, multiple suction cycles may take place within a single heating cycle. The amount of time and the temperature at which heat is applied can be varied. Further, the amount of time and magnitude at which a pressure differential is applied can be varied. Each is varied and applied so as to (1) substantially eliminate any damage to the eye and (2) permanently change the shape of a component of the eye to correct the point at which the eye focuses light thereby resulting in improved vision for the patient. To accomplish such the apparatus may remain in contact with the eye between therapeutic applications, or may be removed between applications.

A preferred embodiment of the invention uses a moving heated fluid to raise the temperature of a selected area of the cornea. Preferably, the fluid is an aqueous saline solution having a pH and ion concentration in osmotic balance with the cornea. The temperature of the fluid must be sufficient to allow the collagen fibrils to creep at a reasonable rate, but must not be sufficiently high as to result in collagen shrinkage. Preferably, the temperature is between 45° C. and 55° C. for a human eye. An alternative embodiment of the invention uses an infrared radiation source to raise the temperature of a selected area of the cornea. In a preferred embodiment, the heating is applied for a period of 1–3 minutes in each heating cycle.

The invention features a vacuum manifold for the application of a pressure differential to the eye. In a preferred embodiment, the magnitude of suction applied is between 100 mmHg and 500 mmHg. Suction may be applied for a period of between 1 second and 3 minutes. In a more preferred embodiment, the suction is applied for a period of 15–30 seconds in each suction cycle.

A primary object of the invention is to provide a method of altering the shape of one or more components of an eye which is preferably a human eye by heating a predetermined heating zone of the eye to a therapeutically effective temperature which is below the collagen shrinkage temperature of the cornea and applying a therapeutically effective amount of pressure (e.g., vacuum) to the eye in order to stretch a component of the eye such as the cornea, a predetermined amount thereby permanently altering the shape of the eye in a manner so as to improve the focus of the eye and the patients resulting vision.

Another object of the invention is to provide such a method wherein the heating is carried out by the flow of a heated fluid such as an aqueous saline solutions and/or by the application of other heating means such as electromagnetic radiation which may be infrared radiation in amounts so as to raise the temperature of the heating zone to a temperature in the range of about 45° C. to about 55° C. for a period of time in the range of about 1–5 minutes.

An advantage of the invention is that the shape of the eye can be changed so as to correct vision without cutting any of the components of the eye.

Another object of the invention is to provide a device for changing the shape of the eye and particularly for changing the shape of the cornea of the eye, which device is comprised of a manifold having an outwardly extending surface which conforms to the outer surface of the eye in a manner so as to create a seal between the eye and the extending surface, which manifold includes an open channel leading to a first opening in the manifold wherein the channel is connectable to a vacuum source and further wherein the manifold is preferably connectable to a heating source which may be an electromagnetic heating source or a fluid pumping source.

It is an object of the present invention to provide a method for changing the curvature of the eye or component thereof such as the cornea sufficiently to correct or reduce refractive errors of the eye by a non-invasive and nondestructive procedure, leaving the eye intact and undamaged.

It is another object of the invention to provide an apparatus for the non-invasive, nondestructive therapeutic application of heat and suction to correct or reduce refractive errors of the eye.

An advantage of the invention is improved post-treatment stability, strength, and clarity.

A feature of the invention is that it may be practiced on an eye that has undergone pretreatment.

These and other objects, advantages and features of the present invention will become apparent to those skilled in the art upon reading the disclosure.

DESCRIPTION OF PREFERRED EMBODIMENTS

Figure 1:
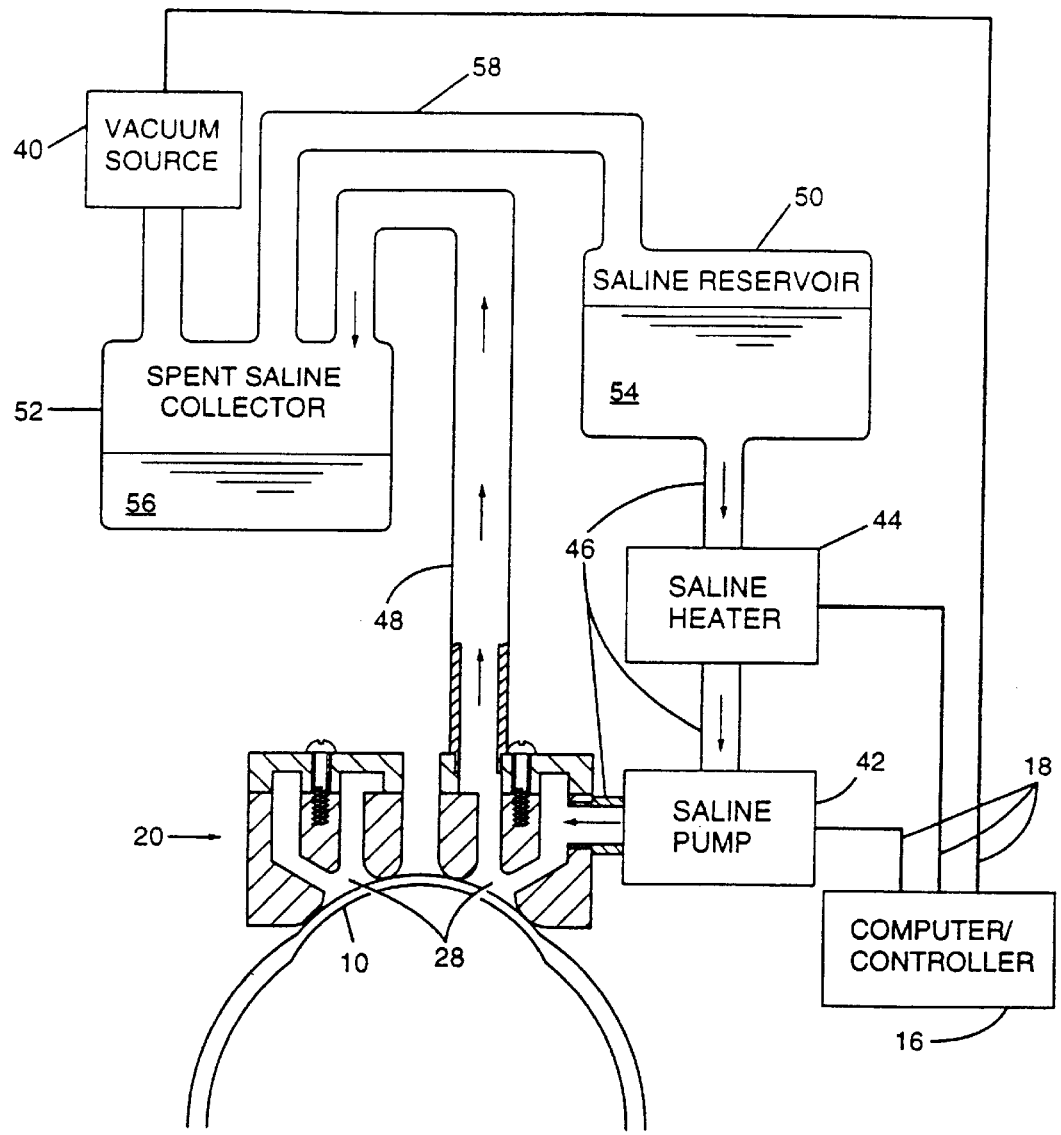
FIG. 1 is a schematic, cross-sectional view of the device of the invention using fluid heating applied to the cornea of an eye.

Before the present invention is described, it is to be understood that this invention is not limited to particular materials, methods, or processes as such may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "an", and "the" include plural referents unless the context clearly dictates otherwise. Thus, for example, reference to "a fluid" includes mixtures of more than one fluid, and reference to "a treatment cycle" includes multiple rounds of such cycles.

The publications discussed herein are provided solely for their disclosure prior to the filing date of the present application. Nothing herein is to be construed as an admission that the present invention is not entitled to antedate such publication by virtue of prior invention.

Unless defined otherwise, all technical and scientific terms herein have the same meaning as commonly understood by one of ordinary skill in the art to which this invention belongs. Although many methods and materials, similar or equivalent to those described herein, can be used in the practice or testing of the present invention, the preferred methods and materials are described herein. All publications cited herein are incorporated herein by reference for the purpose of disclosing and describing specific aspects of the invention for which the publication is cited in connection with.

Definitions

The term "creep" as used herein refers to a continuous increase in strain (particularly of a component of the eye and more particularly of collagen fibrils of the cornea) at a given level of stress, where the rate of strain increase with time ("creep rate") is a function of temperature and applied stress. Creep is distinct from ordinary plasticity in that creep can occur even at stresses within the elastic range of the material. Creep can be divided into primary creep, which is fully recoverable upon removal of the load, and secondary creep, which results in a permanent, unrecoverable residual strain. The term creep as used herein refers specifically to secondary creep unless otherwise indicated. Furthermore, since collagen fibrils do not support compressive loads, the creep of collagen fibrils results from tensile stresses, leading to elongation of the fibrils. The elongation obtained via the invention is, at least in part, a permanent elongation. It is understood that nothing is permanent and such is particularly true of living tissue. Accordingly, the "permanent" change per the invention is a change which remains for more than a few hours or days but rather remains for several months, or more preferably over several years or the life of the patient.

The term "treatment cycle" as used herein refers to a specific period of time of a therapeutic application for stretching the cornea, including periods of heating, suction, rest, and cooling. To achieve the desired amount of cornea stretching, one treatment cycle may be applied, or multiple treatment cycles may be applied. A specific treatment cycle is depicted in FIG. 6.

The term "fluid" as used herein refers to any flowable material that may be heated to the desired temperature with a sufficient ability to pass through the ports of the apparatus of the invention. The fluid must substantially maintain the osmotic balance of the eye, and be of acceptable pH range. Preferably, the fluid is a balanced salt solution of the kind conventionally used in the irrigation of the eye. The term fluid encompasses liquids, gels, emulsions, suspensions, gases, vapor, etc. The fluid should be sterile and may contain anti-bacterial agents and preservatives in small concentrations.

The term "therapeutic temperature" as used herein refers to a temperature at which the desired rate of creep is induced, resulting in a permanent change in the cornea shape and thus the focus of the eye. The therapeutic temperature of the preferred embodiment is between 37° C. and 60° C., and more preferably between 45° C. and 55° C., although other sufficient temperatures may be used. The therapeutic temperature should not exceed the collagen shrinkage temperature, however, since shrinkage of the collagen fibrils produces results counter to the desired stretching. There is not a unique therapeutic temperature, since a desired amount of creep can be achieved by many combinations of temperature, stress, and time.

The term "pressure differential" refers to a change in the pressure distribution at the surface of the eye, causing a deformation of the cornea. Such a pressure differential could be due to a force applied by a solid object or to a change in fluid pressure at the surface of the eye. The pressure differential may cause an increase of pressure at the surface of the eye, such as the application of mechanical contact pressure, or the reduction of pressure, such as the application of suction. In the preferred embodiment, the pressure differential applied to the eye is a combination of a reduction of pressure within the suction zone and an increase in pressure within the contact zone.

The term "therapeutic level of suction" refers to a magnitude of suction at which a desired rate of creep is induced at the elevated temperature. The therapeutic level of suction for the preferred embodiment is between 100 mmHg and 500 mmHg (generally at a temperature of from 37° C. to 60° C.), but other sufficient levels reasonable to those skilled in the art may also be used, up to and including a complete vacuum (760 mmHg). The therapeutic level of suction will vary with the temperature, vacuum port configuration, desired amount of creep, and desired length of treatment time.

The term "therapeutic pressure differential" refers to a magnitude of pressure differential at which a desired rate of creep is induced. In the preferred embodiment, the pressure differential is induced by the application of suction via a vacuum manifold. In such a case, the therapeutic pressure differential is that pressure differential induced at the therapeutic level of suction. From considerations of static equilibrium, the downward force on the manifold due to vacuum, gravity, and applied load (from the practitioner) must be balanced by the upward force due to contact pressure.

DETAILED DESCRIPTION OF THE PREFERRED EMBODIMENTS

Collagen fibrils are the main load-carrying elements in the cornea and in many other tissues (e.g. tendon) and much basic groundwork has been laid with regard to the thermomechanics of collagen. At temperatures beginning just above core body temperature (37° C. for humans), there is an abrupt change in the stress-strain behavior of collagen fibrils, manifested by abruptly increased rates of stress relaxation and creep (under tensile stress). The shrinkage temperature of collagen fibrils, corresponding to the molecular transition from a triple helix to a random coil configuration, is perhaps 20° C. higher than core body temperature, depending on the animal species as well as the specific tissue. In general, the shrinkage temperature is about 58–60° C. for tissue in its natural state, although shrinkage temperatures as low as 55° C. have been reported for human corneas. Thus, there is a range of corneal temperature from about 37° C. to about 60° C. that allows greatly increased rates of creep without causing thermal breakdown of collagen fibrils. It should be noted that the normal temperature of the cornea is less than core body temperature by about 2° C. due to natural convective and evaporative cooling, although this varies of course with the surrounding environment.

The precise chemical mechanism of creep in collagen-dominated tissue is still unknown. However, the rate of creep increases greatly with increasing temperature and with increasing stress, characteristic of a thermally-activated rate process. The application of stress need not be continuous for a cumulative effect of temperature, stress, and time to occur (Ku and Greene, *American Journal of Optometry & Physiological Optics*, 1981, v. 58, pp. 528–535). That is, a given amount of creep can be accomplished by either one extended application of a given stress or many brief applications of such stress, assuming the temperature is one within the proper range. Likewise, a given amount of creep can be achieved by a short application of stress at one temperature or a longer application of the same stress at a lower temperature.

The present invention exploits the creep properties of the collagen fibrils in the cornea for therapeutic purposes, in the temperature range from just above normal physiological temperature to the thermal shrinkage temperature of collagen. Creep resulting from specific applications of sufficient stress and sufficient temperature for sufficient time leads to a permanent new shape of the cornea. If the creep is concentrated primarily in the paracentral and peripheral cornea (the annular region from 4 mm to 11 mm diameter) and in the circumferential direction, then the central cornea flattens, thus reducing the dioptric power of the cornea, tending to correct myopia. On the other hand, if the creep is concentrated in the paracentral and peripheral cornea and is primarily in the radial direction, the central cornea steepens (becomes more curved), thus increasing the dioptric power of the cornea, tending to correct hyperopia. If creep is concentrated primarily in the paracentral cornea and in the circumferential direction, but restricted to the vicinity of a particular meridian, the curvature of the central cornea becomes flatter in the central segment of that meridian, tending to correct astigmatism where said meridian is too steep.

The method of the present invention involves the heating of certain selected areas of the eye, either by the application of a heated fluid or by the application of infrared (IR) radiation to these selected areas. In the case of a heated fluid, the fluid is preferably an aqueous saline solution, in osmotic balance with the cornea to prevent either a hypertonic or hypotonic response. In the case of IR radiation, the energy is preferably primarily in the region of the spectrum with wavelength longer than 1400 nm. Preferably, the target temperature of the cornea exposed to heating is between 37° C. and 60° C., and more preferably between about 45° C. and 55° C.—it being noted that normal temperature for the cornea is about 35° C. depending on conditions. The temperature of the eye must not, however, be sufficient to induce shrinkage of the collagen fibrils. The heating is preferably applied for periods of between 1 and 3 minutes.

The method of the invention also involves the application of a pressure differential to certain selected areas of the eye to deform the shape of the eye. The area of the eye to which a pressure differential is applied may be coincident with the area exposed to heating, or it may be a superset. Preferably, the pressure differential is a combination of a reduction of pressure, due to a partial vacuum, at one portion of the cornea and an increase in pressure, due to contact pressure from a vacuum manifold body, at another portion of the cornea.

In a preferred embodiment, the application of heating and application of the pressure differential are repeated in a determined set of applications of heating and pressure differential. The sets may be repeated a plurality of times, until the desired change in corneal shape is achieved.

In an apparatus of the present invention, a heated fluid is directed over selected areas of the cornea by way of a manifold structure in contact with the cornea. The manifold structure has a surface that conforms to the shape of the surface of an eye extending from the manifold. The surface is shaped such that it can contact the eye and form a seal between the eye and the extended surface of the manifold. The apparatus for heated fluid has one channel leading to the manifold, and another channel extending from the manifold. Each of these channels is connected to the manifold through openings in the manifold structure.

The surface extending from the manifold is preferably constructed of two smooth, concentric surfaces. When in contact with the eye, the area between the two surfaces defines the region of the eye subjected to the application of heating and/or pressure differential. This annular region is the treatment zone of the cornea, which contains the areas of the cornea subject to heat and applied pressure.

The apparatus may also include a means for pumping fluid into the first channel, into the space(s) created by the contact of the manifold structure to the eye, and out through the second channel. The means for pumping the fluid may be integrated with a fluid heating means, or the fluid heating means may be separate. In addition, a means for applying a pressure differential to the area between the manifold surface and the eye many be included in the apparatus. This pressure means may be attached to the means for pumping fluid, or may be separate.

FIG. 1 shows a system in accordance with the invention, utilizing a manifold structure 20, shown in cross section, and conventional elements shown schematically. The apparatus connects controllable vacuum means 40 and fluid heating means 44 to manifold structure 20. Although in the preferred embodiment of the invention, the vacuum means 40 and fluid heating means 44 are connected, the invention may alternatively have physically separate means for application of vacuum and heating.

When manifold structure 20 is placed in proper position on a cornea 10, a closed pathway connects a fluid reservoir 50 to a fluid collector 52. Fluid reservoir 50 contains a fluid, preferably isotonic saline in a balanced salt solution (BSS), for the purpose of heat transfer to and from selected regions of cornea 10. Other fluids may be used, but each should present low toxicity to the cornea, not boil at the vacuum levels and temperatures used, and acceptably maintain the hydration of the cornea. The reserve fluid 54 flows from reservoir 50 through inflow tubing 46 to a controllable flow-through saline heater 44, then through further tubing 46 to a controllable saline pump 42, then through further tubing 46 to manifold structure 20. The initial temperature of reserve fluid 54 is lower than the therapeutic temperature to allow the fluid to be used for cooling when the heater is shut off. After having passed through manifold 20, the fluid flows out through fluid outflow tubing 48 into spent fluid collector 52, which collects spent fluid 56. The entire volume of the fluid path is under the influence of a controllable partial vacuum created by controllable vacuum pump 40, shown connected to collector 52. The vacuum pressure in reservoir 50 and collector 52, both of which are closed off from the atmosphere, is equalized by a connecting pressure equalizing tube 58. This arrangement of heater, pump, and tubing is that of the preferred embodiment of the invention, but can be altered as may be apparent to those skilled in the art. For example, the pump can be placed upstream of the heater, or the heater and pump can be combined into a single unit. The control of the vacuum pump, fluid pump, and fluid heater is preferably carried out by a central computer or controller 16, connected to the controllable elements by wiring 18, and responsive to the input of the practitioner.

Figure 2A:
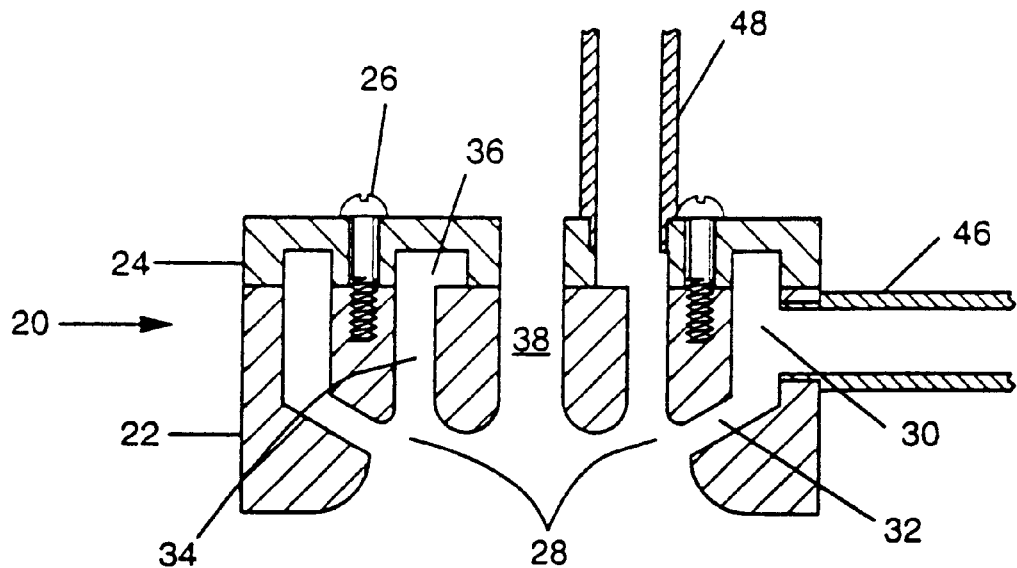
FIG. 2A is a cross section of a preferred manifold structure for application of a moving heated fluid and vacuum pressure.

FIG. 2A shows a cross section of manifold 20, which is a generally cylindrical body having a lower face which forms a cornea-receiving concavity containing port or ports 28 with outer surfaces, or edges, that conform substantially to the original shape of the cornea. Upon entering manifold 20, the saline is distributed via annular inflow channel 30 to several inflow bores 32, through the chambers formed by the contact of the cornea with ports 28, then through outflow bores 34 into annular outflow channel 36, and through the outflow tubing 48.

The material of manifold 20 is preferably stainless steel, but can be any solid material of sufficient stiffness and strength, e.g. another metal or plastic. For ease of manufacture and cleaning, the preferred embodiment of manifold 20 has two separable parts, shown in FIG. 2A as manifold base 22 and manifold cap 24, joined by cap attachment screws 26. This two-part construction also allows for the interchangeability of manifold bases with various shapes. For example, a selection of manifold bases sized to fit a range of sizes and shapes of corneas, and with configurations to treat various refractive conditions, may be provided in order to accommodate different patients. Manifold cap 24 is a disk containing annular fluid outflow channel 36 and the upper portion of annular fluid inflow channel 30. The upper portion of manifold base 22 contains the lower portion of annular inflow channel 30. Manifold structure 20 also contains central through-bore 38 to provide atmospheric pressure to the central cornea and to aid in visualizing the central cornea. A handle (not shown) may be provided on the manifold to aid in proper placement on the eye.

Figure 2B:
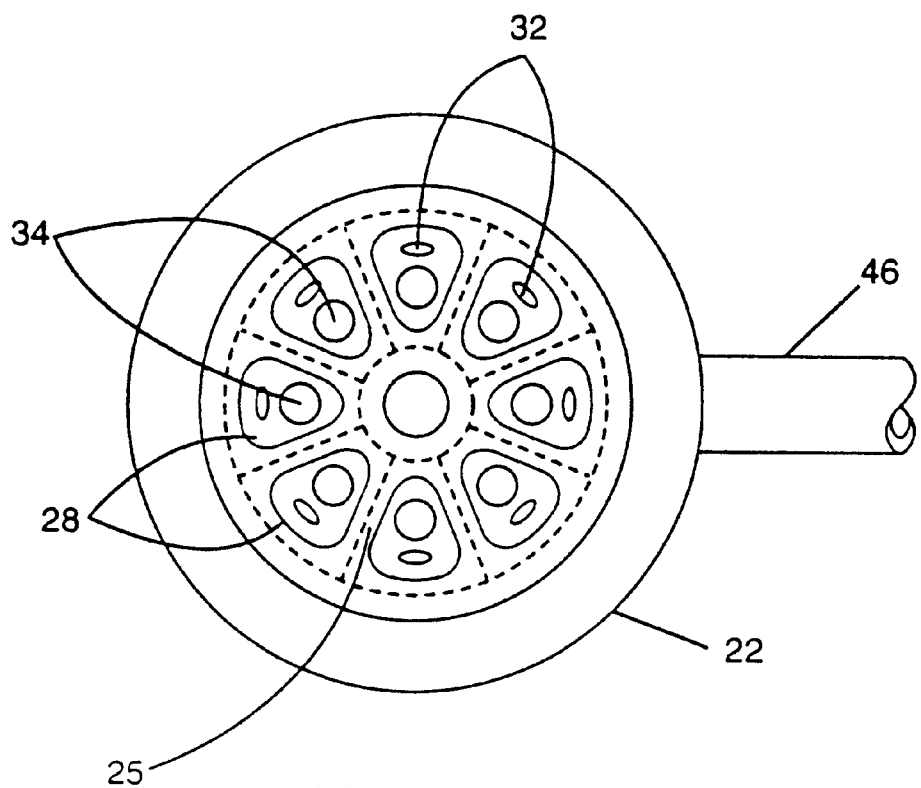
FIG. 2B is a plan view of a vacuum port configuration for circumferential stretching, showing eight identical vacuum ports in a circumferential array. The vacuum ports are configured for circumferential stretching.
Figure 3:
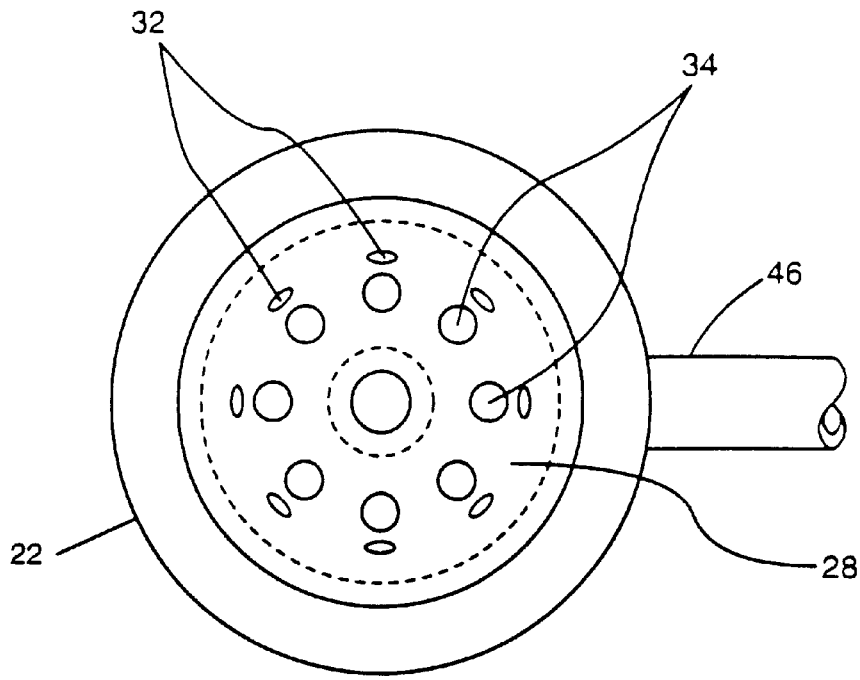
FIG. 3 is a plan view of a vacuum port configuration for radial stretching, showing a single annular vacuum port.
Figure 4:
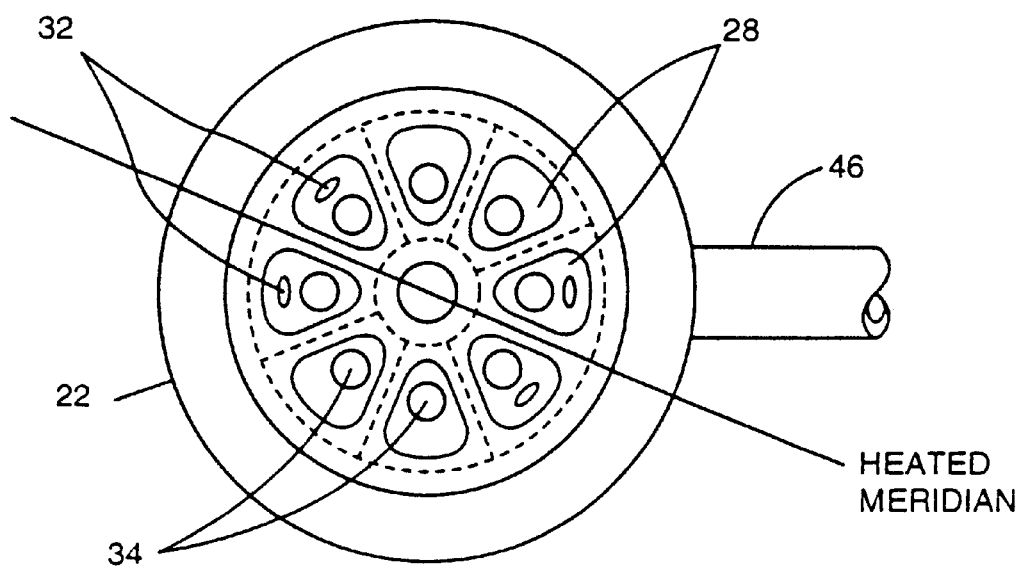
FIG. 4 is a plan view of a vacuum port configuration for nonsymmetric circumferential stretching, showing four vacuum ports with fluid inlet ports, and four vacuum ports without fluid inlet ports, and indicating the heated meridian.

The shape of ports 28 can be partly characterized by the points of initial contact with the cornea, shown as dashed lines superimposed on FIGS. 2B, 3, and 4. FIG. 2B, a manifold for myopia correction, shows eight identical ports, each port defined by a 45° sector of the annulus formed by the inner and outer circles of initial contact, where the angle is defined by cornea-contacting webs, spokes, or struts 25. The edges of ports 28 that contact the cornea are preferably rounded, or filleted, because edges that are too sharp may cause excessive bending of the cornea under the influence of the vacuum and result in damage to the endothelium. In FIG. 2B, each port 28 connects with one inflow bore 32 and one outflow bore 34.

Another number of ports may be used for myopia correction, but ports that are too small will not have sufficient membrane stretching power, and ports that are too large (angle between struts is too large) will stretch the cornea primarily in the radial direction. The dimensions of each port should be large relative to the corneal thickness, which is about 0.5 mm. As a result of these considerations, the number of ports used for myopia correction is preferably six to nine, and more preferably seven or eight.

FIG. 3 shows a plan view of the lower face of manifold base 22 for the correction of hyperopia. In this case, there is a single annular port 28 connected to a plurality of inflow bores 32 and outflow bores 34. The points of initial contact with the cornea form two concentric circles, as shown by the dashed lines.

FIG. 4 shows a plan view of the lower face of manifold base 22 for the correction of astigmatism in the case where a meridian of the eye is too steep. This astigmatism-correcting manifold base contains eight ports 28 separated by radial struts 25, but only four of the ports connect with fluid inflow bores 32: one pair surrounding each of the two ends of the "heated meridian".

Figure 5:
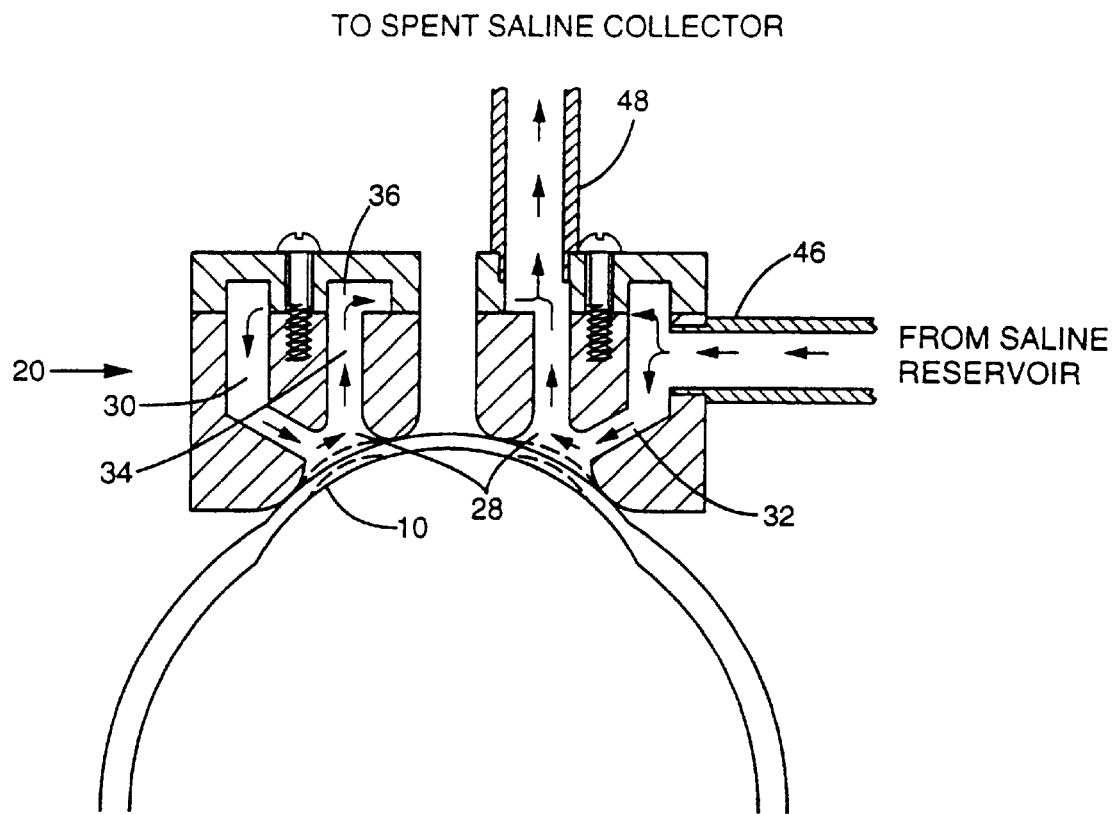
FIG. 5 is a cross section of the preferred manifold structure of FIG. 2A applied to the cornea of an eye, and illustrating some aspects of the operation of the invention.

The imposition of a vacuum within the manifold causes the cornea to bulge into the chamber formed by the contact of each port with the cornea, as shown in FIG. 5. In the case of the myopia-correcting manifold of FIG. 2B, this deformation implies that the cornea is indented by the rounded edges of each port, including the radial struts. Considering a circumferential path at a radius within this suction zone, the effect is to create a series of bulges and indentations along this path. Circumferential stretch arises due to the longer length of this sinuous path compared to the circumference of the undeformed cornea at the same radial location. Symmetry considerations imply that there will be no circumferential slip across the struts, but radial slip is not so constrained. Consequently, for the myopia-correcting manifold, there is relatively little radial stretch, since additional radial lengths of cornea are drawn into the port chamber to accommodate the bulging.

In the case of the hyperopia-correcting manifold of FIG. 3, there are no radial struts, but rather one single annular port. As a consequence, an initially circumferential path within the suction zone remains relatively undeformed under the influence of vacuum rather than deforming into a sinuous series of bulges and indentations. Therefore, there is relatively little circumferential stretch. Instead, the imposed pressure differential is accommodated by increased radial stress (and stretching). This radial stress occurs both within and outside of the suction zone, so that the concentration of radial creep within the suction zone occurs primarily due to the higher corneal temperature there during heating.

The configuration of port or ports 28 determines the portion of cornea 10 subject to direct heating and suction, called the heating zone and suction zone, respectively. For fluid heating means, the heating zone is that portion of the cornea subject to flowing, heated fluid. FIG. 5 provides a general schematic for the fluid flow when the invention is in practice. In the case of radiant heating, the heating zone is that portion of the cornea exposed to radiation. The suction zone is that portion of the cornea subject to vacuum, or suction. Essentially, the suction zone is that portion of the cornea contained within the points of initial contact of port or ports 28, shown as dashed lines in FIGS. 2B, 3, and 4. In the case of FIGS. 2B and 3, the heating zone and suction zone are coincident. For correction of astigmatism, where nonuniform stretching is desirable, not all vacuum ports provide for heating, thus the heating zone differs from the suction zone, as in FIG. 4. The boundaries of the heating and suction zones change somewhat as the cornea deforms due to an increasing pressure differential. In particular, the contact zone (the portion of the cornea contacting the manifold) increases in area and the heating and suction zones become smaller.

Figure 6A:
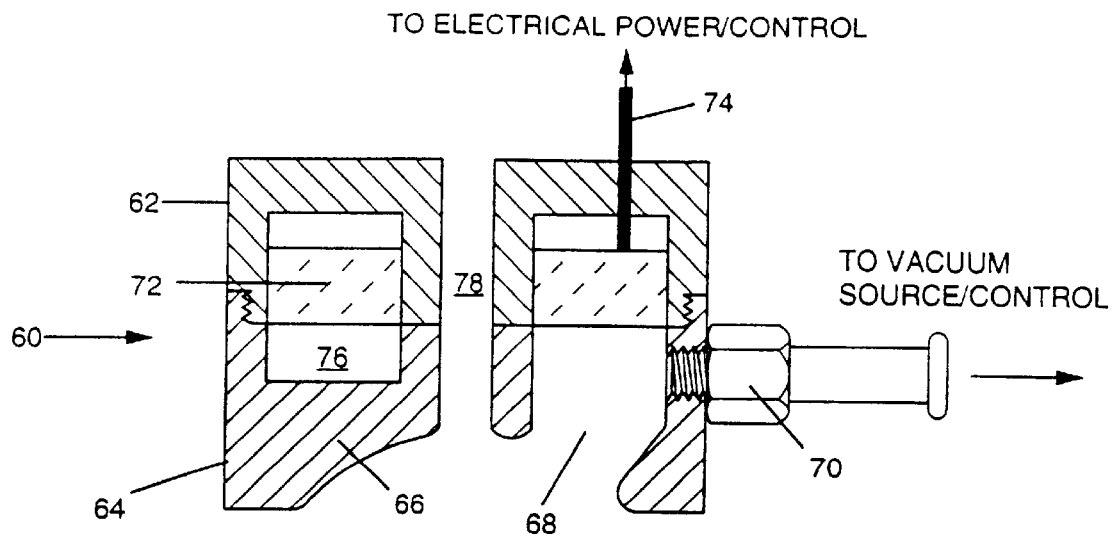
FIG. 6A is a cross section of a preferred manifold structure for application of radiant heating and vacuum pressure.

Referring now to FIG. 6A, a preferred embodiment for using radiant heating is shown. In the infrared (IR) region of the spectrum, the cornea exhibits a broad absorption peak extending from about 2700 nm to 3300 nm wavelength and centered at a wavelength of about 3000 nm (corresponding to the O—H stretch mode of water). Furthermore, for infrared radiation with wavelengths greater than about 1400 nm, very little of the energy is transmitted to the interior structures of the eye. Consequently, the cornea can be efficiently heated either by conventional infrared means or by a laser operating at a wavelength in the absorption band. Approximating a conventional IR source as an ideal blackbody with a surface temperature of 726.85° C. (1000 K), the peak emissive power is at 2900 nm, and 99.1% of the total emissive power is at wavelengths greater than 1400 nm. The spectral character of the emitted radiation can be further refined by a bandpass or notch filter, such as a "cold mirror". Conventional IR sources which can be used in the invention include high-temperature alloy wires or ribbons, etched-foil panels, ceramic, or "quartz element" heaters. Preferably, an etched-foil panel is the emitting element. This preferred IR source can be configured for compact size, low thermal mass, and fast warmup time (5–10 seconds). These properties are important because they allow the IR source to be switched alternately on and off in a "duty cycle" (determined by prior experiment) during the heating cycle to maintain the desired therapeutic temperature of the cornea without overheating it. In the preferred embodiment, the IR source is configured for an emissive power of about 1–2 W/cm$^2$ (while on), although the irradiance at the cornea is less due to geometric considerations. The IR heating method allows for the use of masks to control the geometric distribution of IR radiation onto the surface of the cornea. In the case of astigmatism correction, for example, an opaque mask may be used to prevent heating of the cornea in certain ports.

FIG. 6A shows a manifold structure 60, with manifold cap 62 and manifold base 64. Manifold cap 62 contains a controllable IR source or emitter 72 connecting with external power/control via wiring 74. Base 64 contains ports 68 communicating with vacuum means via an annular vacuum distribution channel 76 connected to vacuum fitting 70. Because of an odd number of ports 68, the cross section of cornea-contacting radial strut 66 is visible. A through-bore 78 is provided to aid in visualizing the cornea center.

Figure 6B:
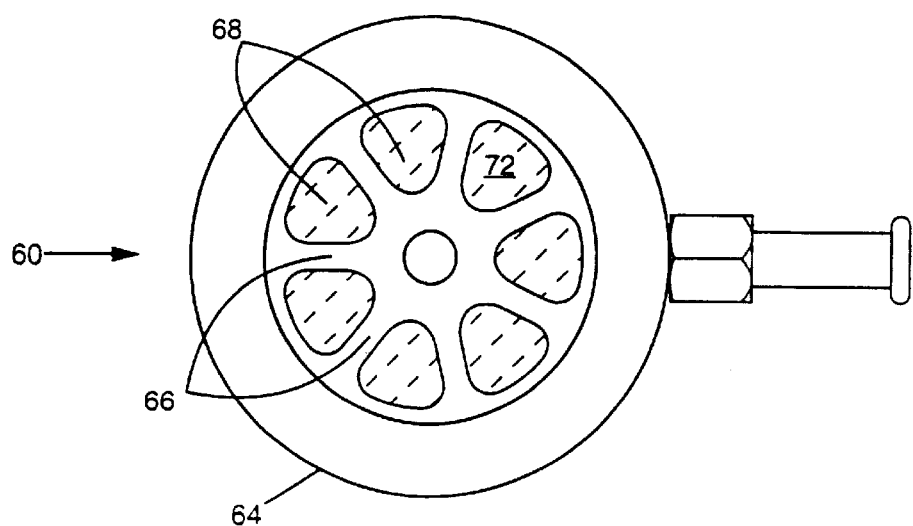
FIG. 6B is a plan view of a vacuum port configuration for circumferential stretching, showing seven identical vacuum ports in a circumferential array. The vacuum ports are configured for circumferential stretching.

FIG. 6B is a plan view of manifold base 64, which is configured to correct myopia. Seven identical ports 68 are arranged in a circumferential array, each port exposed to the radiation of the IR emitter. Ports 68 are separated by cornea-contacting radial struts 66.

Since the various structures of the eye conduct heat, it is preferred to alternate periods of heating with periods of cooling to avoid overheating of the interior structures of the eye. Referring to FIG. 1, this is accomplished by switching off heater 44 while maintaining the flow of cooler fluid 54 over the heating zone. Alternatively, as in the case of IR heating, the manifold structure may be removed from the eye and the eye irrigated with sufficiently cool saline or simply allowed to undergo cooling by natural convection and evaporation.

The determination of the allowable heating period depends on the configuration and size of the heating zone, the chosen therapeutic temperature, and the heat transfer efficiency of the heating method. One way to establish a safe maximum heating period is to limit the temperature of some interior structure of interest to be below some critical level, assuming ideal heat transfer efficiency, i.e., that the corneal surface within the heating zone is held constant at the therapeutic temperature. For example, the allowable heating period can be determined as the length of time needed to heat the lens of the eye to a temperature of 41° C., given a particular heating zone configuration, therapeutic temperature, and initial physiological temperature. It follows that the allowable heating period in the case of a 50° C. therapeutic temperature is shorter than the allowable heating period for the case of a 45° C. therapeutic temperature for the same heating zone. These time limits are preferably determined by both calculation and experiment.

The vacuum level is preferably raised and lowered cyclically to allow for sufficient vascular perfusion of the eye. Application of vacuum raises the intraocular pressure (IOP), and excessive IOP can occlude the arteries and veins within the globe, reducing or stopping the flow of blood to critical visual structures. It is critical to the health of the eye that periods of reduced perfusion not be excessive. Thus, the level of vacuum is controlled to be either a minimum level V1 or a therapeutic level V2. For example, V1 may be 30 mmHg and V2 may be 300 mmHg.

The determination of the allowable suction period depends on the IOP induced by a particular manifold configuration and therapeutic level of suction. In general, a higher induced IOP restricts vascular perfusion more than a lower induced IOP. IOP can be monitored by scleral tonometry during the application of the manifold, and the therapeutic level of suction (or time of application) adjusted so that, for example, the IOP does not exceed 65 mmHg for more than a few seconds. Artificially induced high levels of IOP decay over a short time due to the increased net outflow of aqueous humor from the eye, so the therapeutic level of suction may be increased during a suction period rather than remain constant.

Figure 7:
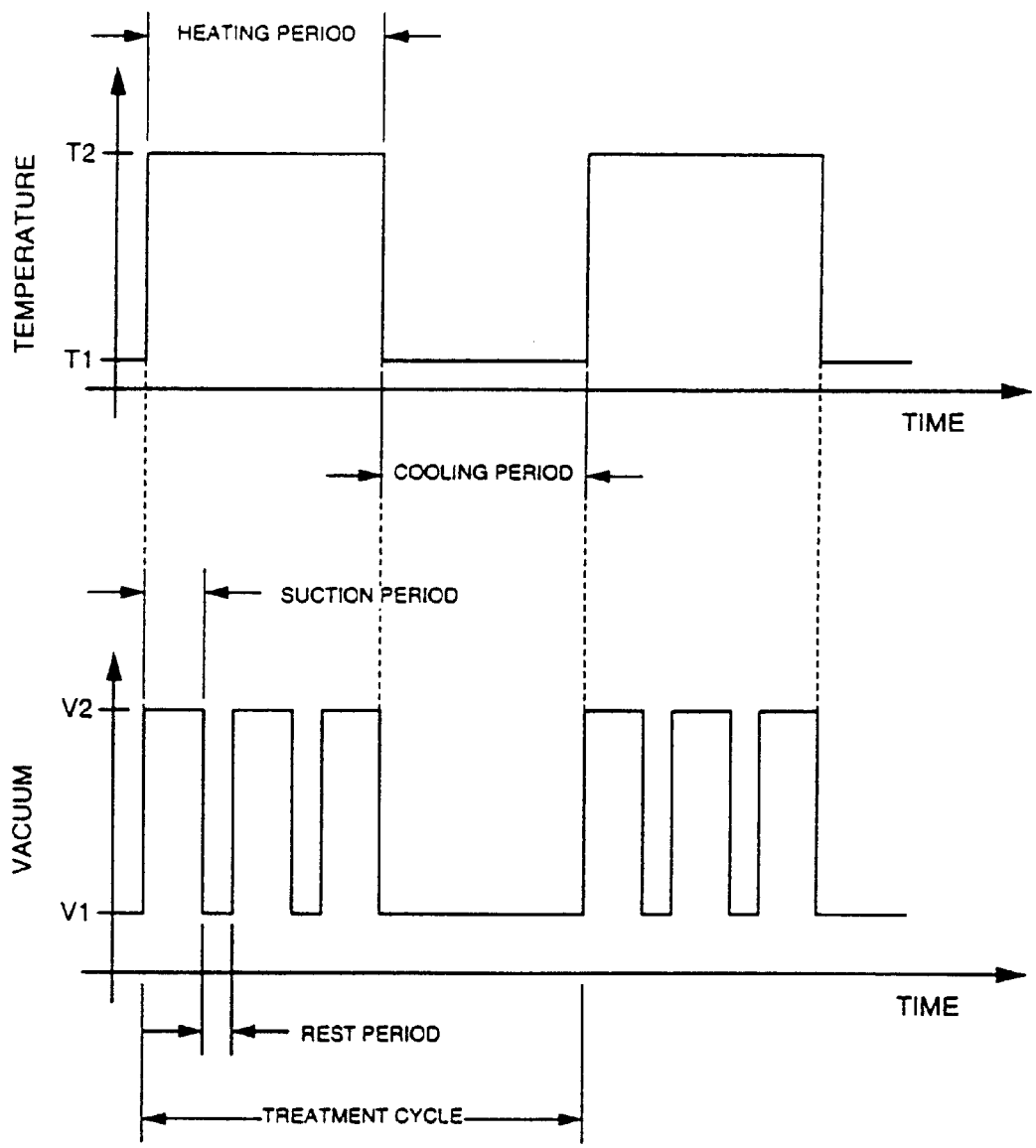
FIG. 7 is a timing diagram for the control of vacuum pressure and corneal heating zone temperature.

A timing diagram for the operation of the invention after the manifold structure is properly placed on the cornea is shown in FIG. 7. Previously determined safe durations of heating and vacuum are shown as heating period and suction period, respectively. Levels of target corneal temperature and vacuum are shown along the same time scale. For simplicity, these two parameters are shown to vary abruptly between lower and upper limits, although of course a certain amount of time, e.g. a few seconds, is needed to establish each level due to considerations of thermal mass and finite volume effects. The beginning of a cycle of treatment is marked by heating the corneal heating zone to therapeutic temperature T2 from the its initial temperature T1, which may be the physiological temperature. After a short delay to allow sufficient temperature rise in the corneal heating zone, the level of vacuum is raised to a therapeutic level of vacuum V2 from a minimum level V1. After a suction period has elapsed, the vacuum is reduced to minimum level V1 and a rest period is allowed to elapse. FIG. 7 shows three suction periods during a single heating period, but there can be more or fewer depending on the relative duration of an allowable heating period to that of an allowable suction period. Multiple heating periods within a single suction period, however, are not preferred, since there is little or no contribution to the desired corneal creep during the cooling periods. Therefore, in cases where the allowable suction period exceeds the allowable heating period, the shorter period is used, taking into account the delay for temperature attainment at the beginning of each heating period. Also, although FIG. 7 shows two uninterrupted treatment cycles, the manifold structure may also be completely removed from the eye following any treatment cycle to allow for measurements of corneal topography and temperature.

The subject eye of the invention is an eye, either in its natural state or in a pretreated condition and may be the eye of any mammal, e.g., cat, dog, pig, horse, but is preferably a human eye. The information provided here such as temperature and pressure are for a human eye and could be adapted based on the disclosure to other animals. Possible pretreatments include removal of the epithelium, reduction of the intraocular pressure, application of an enzyme or other softening agent, and application of an anesthetic. It should be noted that some chemical agents can change the collagen shrinkage temperature, so the therapeutic temperature in such cases must be appropriately adjusted. Other pretreatments include other refractive procedures, such as RK, PRK, and LASIK, assuming sufficient time for wound healing has elapsed. Also, pretreatment may include the application of a lubricant or sealant before applying the manifold.

To preserve the sterility of the device between patients, the manifold and associated tubing may be made of materials that can be exposed to many rounds of sterilization. Alternatively, the manifold and associated tubing may be prepackaged in a sterile state and disposable following use on a patient. Such disposable sterile items may also be composed of any suitable material, such as metal, rubber, plastic, etc. Another approach to sterility and interchangeability uses a disposable covering on the manifold base, where the disposable covering determines the geometry (e.g., radius of curvature) of the cornea-contacting port edges. In addition, a disposable manifold cover may be made of material that is more compliant than the manifold body, thus allowing for slight imperfections in the fit and sealing with the cornea.

The amount and distribution of creep in the cornea are strongly influenced by the magnitude and geometric distribution of the therapeutic temperature, the magnitude and geometric distribution of pressure differential applied, and the length of treatment time. Furthermore, the final shape attained by the cornea is a function of both the creep distribution and the normal-temperature stress-strain response of the treated cornea to the normal intraocular pressure. A precise determination of this final shape requires detailed knowledge of the thermal creep function of the cornea (creep rate as a mathematical function of temperature and stress) as well as the nonlinear constitutive law for the cornea at normal physiological temperature. These functions may be ascertained to some extent by, for example, thermomechanical testing on cadaver eyes or corneas, but it is anticipated that remaining uncertainties may best be resolved by corneal topography measurements before, during, and after applying the inventive method to living eyes. In addition, corneal topography must be correlated to actual refraction of the eye by standard visual testing of patients.

Figure 8:
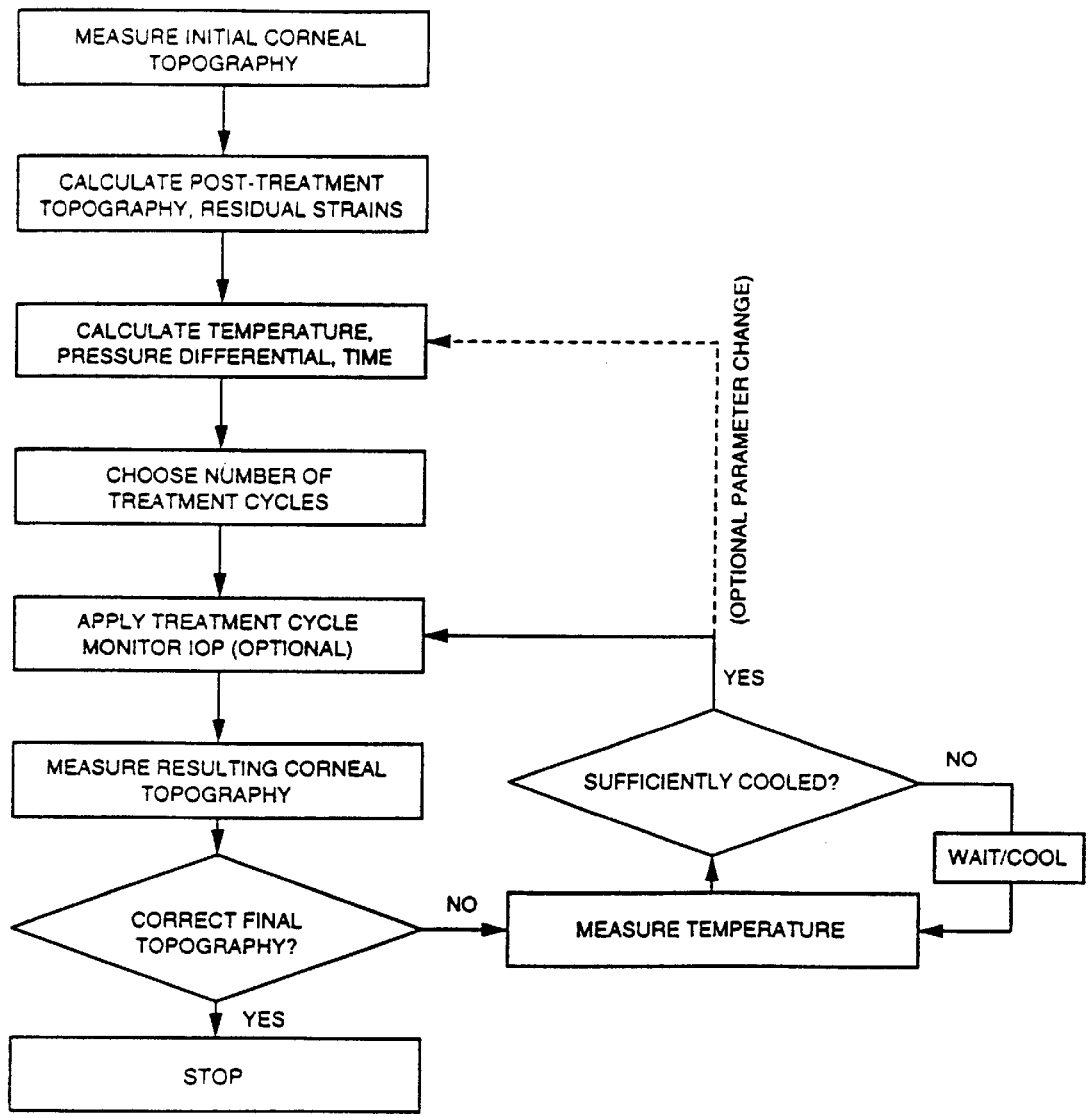
FIG. 8 is a flow chart pointing out procedures surrounding the inventive method.

Therefore, a preferred mode of application of the inventive method utilizes a pre-treatment corneal topography measurement and the calculation of an ideal post-treatment corneal topography from optical considerations (such as central corneal curvature or ray-tracing analysis). The difference between the measured pretreatment shape and the calculated post-treatment shapes implies a certain distribution of creep in the treated cornea. Using a finite-element technique, along with the creep function, constitutive law, manifold geometry, a treatment plan of temperature, pressure, and time can be formulated. This treatment plan can then be divided into perhaps ten (10) treatment cycles, allowing for the measurement of corneal topography in between treatment cycles, assuming the manifold is removed. This division also allows the practitioner to accommodate individual variations in collagen chemistry among patients, so that, for example, the treatment time can be shortened for a fast-creeping cornea. Such topography information is then compared to the predicted topography at the end of each treatment cycle so that adjustments can be made to the course of treatment. In addition, the removal of the manifold allows the measurement of corneal surface temperature by infrared thermography, which can be used as a guide to assure sufficient cooling of the eye between heating cycles. FIG. 8 provides a flow chart to guide this preferred mode of applying the inventive method.

EXAMPLES

The following examples are put forth so as to provide those of ordinary skill in the art with a complete disclosure of how to carry out the method of the invention and are not intended to limit the scope of what the inventor regards as his invention. Efforts have been made herein to insure accuracy with respect to numbers used (amounts, temperature, time, etc.), but some experimental errors and deviation should be accounted for.

Example 1

Use of the Manifold Device to Correct Myopia (Heated Fluid Method)

To correct myopia, the manifold apparatus is applied to the eye, allowing application of heat and suction through the circumferential array of ports shown in FIG. 2B. A therapeutic application of this configuration causes stretching more along the circumferential direction than the radial direction, leading primarily to circumferential creep and thus to the desired flattening of the central cornea. The initial temperature of the manifold should be near or slightly below the therapeutic temperature, so as to avoid excessive cooling of the cornea during the heating period. As an aid to correct placement, the manifold is visually aligned through the central through-bore to a center mark which has been previously placed on the cornea. A low level of vacuum (about 10–30 mmHg) is applied from the vacuum pump to help hold the manifold in place.

Isotonic saline in a balanced-salt solution is heated and routed over the selected regions of the cornea engaged by the ports of the manifold. The preferred therapeutic temperature of the saline is 50° C., which is below the shrinkage temperature of the collagen of the target eye, and the flow rate is 200 mL/min. The selected regions of the cornea are heated for 30 seconds, and the vacuum pump is adjusted to increase the level of suction from a holding level to a therapeutic level of 300 mmHg. The therapeutic suction draws the engaged regions of the cornea into the vacuum ports, as indicated by dashed lines in FIG. 5. During the application of a therapeutic level of suction, the flow of heated saline is continued in order to maintain the cornea at the therapeutic temperature.

The suction is applied to the cornea in three periods within a single heating period. Specifically, the single heating period of 150 seconds contains, in sequence: the initial 30 second heating (only), a 30 second suction period, a 15 second rest period, a 30 second suction period, a 15 second rest period, and a third 30 second suction period. At the end of the third suction period, both the heat and the suction are decreased from therapeutic levels to allow for a combined cooling/rest period of about 3 minutes. After this cooling/rest period, another treatment cycle begins, which again consists of three suction cycles within a single heating period. Treatment cycles are repeated until the desired corneal stretch is achieved.

Example 2

Use of the Manifold Device to Correct Astigmatism (Heated Fluid Method)

For the treatment of astigmatism, the astigmatism-correcting manifold apparatus is applied to the eye for the application of heat and suction through a circumferential array of ports, aligning the heating meridian of the manifold to the too-steep meridian of the cornea. This treatment configuration leads to a relatively higher rate of circumferential creep under the heated ports, but much less creep under the unheated ports, and thus to the desired nonuniform change in curvature. The treatment cycle parameters follow Example 1.

Example 3

Use of the Manifold Device to Correct Hyperopia

For the treatment of hyperopia, the single annular port of FIG. 3 leads to stretching preferentially in the radial direction, leading primarily to radial creep, and thus to the desired steepening of the central cornea. The manifold apparatus of FIG. 3 is applied to the eye to allow application of heat and suction through the single annular port. A low level of vacuum, preferably about 20 mmHg, is applied to help hold the manifold in place. Isotonic saline is heated and routed over the selected region of cornea engaged to the port of the manifold. The preferred therapeutic temperature of saline is 48° C. The selected region of the cornea is heated for 30 seconds before the vacuum pump is adjusted to increase the level of suction from a holding level to a therapeutic level of 200 mmHg. The suction is applied to the cornea in a single period corresponding to the heating period. Specifically, after the initial 30 second heating period, the therapeutic level of suction is applied for 1 minute. This application of heat and suction is followed by a cooling/rest period of 3 minutes.

Example 4

Use of the Manifold Device to Correct Myopia (Infrared Heating Method)

To correct myopia, the manifold apparatus of FIGS. 6A and 6B is applied to the eye, allowing application of heat and suction through the circumferential array of ports shown in FIG. 6B. A therapeutic application of this configuration causes stretching more along the circumferential direction than the radial direction, leading primarily to circumferential creep and thus to the desired flattening of the central cornea. As an aid to correct placement, the manifold is visually aligned through the central through-bore to a center mark which has been previously placed on the cornea. A low level of vacuum (about 10–30 mmHg) is applied from the vacuum pump to help hold the manifold in place.

The infrared source is operated in a duty cycle to heat the irradiated area of the cornea to the therapeutic temperature. The preferred therapeutic temperature of the cornea is 50° C. for a human eye, which is below the collagen shrinkage temperature of the collagen but high enough to obtain creep. The selected regions of the cornea are heated for 30 seconds, and the vacuum pump is adjusted to increase the level of suction from a holding level to a therapeutic level of 300 mmHg. During the application of a therapeutic level of suction, the operation of the IR source in a duty cycle is continued in order to maintain the cornea at the therapeutic temperature.

The suction is applied to the cornea in three periods within a single heating period. Specifically, the single heating period of 150 seconds contains, in sequence: the initial 30 second heating (only), a 30 second suction period, a 15 second rest period, a 30 second suction period, a 15 second rest period, and a third 30 second suction period. At the end of the third suction period, both the heat and the suction are decreased from therapeutic levels to allow for a combined cooling/rest/measurement period. At this point the manifold is removed and the topography and temperature of the cornea are measured and compared to predicted values. If necessary, after this cooling/rest/measurement period, another treatment cycle begins, which again consists of three suction cycles within a single heating period. Treatment cycles are repeated until the desired corneal stretch is achieved.

The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

List of Reference Numerals 10 cornea of the eye
20 manifold structure for fluid heating
22 base of manifold 20
24 cap of manifold 20
25 radial struts
26 cap attachment screws
28 vacuum port(s) of 20
30 annular fluid inflow channel
32 fluid inflow bores
34 fluid outflow bores
36 annular fluid outflow channel
38 central through-bore of 20
40 vacuum pump
42 fluid pump
44 fluid heater
46 fluid inflow tubing
48 fluid outflow tubing
50 fluid reservoir
54 reserve fluid
52 spent fluid collector
56 spent fluid
58 pressure equalizing tubing
60 vacuum manifold for radiant heating
62 base of manifold 60
64 cap of manifold 60
66 radial strut(s) of 60
68 vacuum port(s) of 60
70 vacuum fitting
72 infrared emitter
74 electrical power and control wiring
76 annular vacuum distribution channel
78 central through-bore of 60

What is claimed is:

1. A method of altering the shape of a subject eye, comprising the steps of:
   (a) heating a predetermined heating zone of the eye to a therapeutic temperature below a collagen shrinkage temperature,
   (b) applying a therapeutic pressure differential within a predetermined treatment zone of the eye, thereby stretching collagen fibrils of the eye in predetermined directions.

2. The method of claim 1, wherein the heating (a) and applying (b) are maintained in a manner so as to permanently elongate collagen fibrils.

3. The method of claim 1, wherein the eye is a human eye, the collagen fibrils are in corneal tissue of the eye and the fibrils are heated to a temperature at or above that required to induce creep of the fibrils resulting in a permanent change in shape of the corneal tissue.

4. The method of claim 1, further comprising the steps of:
   (c) ceasing the applying (b) for a period of time while continuing the heating (a), and (d) repeating the applying (b) for a period of time while continuing the heating (a).

5. The method of claim 4, wherein the ceasing (c) and repeating (d) are carried out a plurality of times.

6. The method of claim 1, wherein the heating is heating by the application of a heated fluid.

7. The method of claim 6, wherein the fluid is an aqueous saline solution.

8. The method of claim 1, wherein the heating is heating by the directing of electromagnetic radiation.

9. The method of claim 8, wherein the electromagnetic radiation is infrared radiation primarily having a wavelength longer than about 1400 nm.

10. The method of claim 1, wherein the therapeutic temperature is in the range of about 37° C. to about 60° C.

11. The method of claim 1, wherein the therapeutic temperature is in the range of about 45° C. to about 55° C.

12. The method of claim 11, wherein the heating (a) is carried out for a period in the range of about 1 to about 5 minutes, and further wherein the pressure differential comprises a reduction of pressure in a predetermined suction zone on a surface of the eye and contact pressure in a predetermined contact zone on a surface of the eye, wherein the pressure in the suction zone is reduced in an amount in the range of about 100 mmHg to about 500 mmHg.

13. A method of changing cornea shape, comprising the steps of:
(a) applying heat to a surface of an eye wherein heat is applied at a temperature and for a time sufficient to induce creep of the eye but insufficient to induce shrinkage of collagen fibrils of the eye;
(b) deforming the shape of the cornea by the application of a pressure differential whereby the deformed shape is maintained after the pressure is removed and the eye returns to body temperature.

* * * * *